United States Patent [19]

O'Connor et al.

[11] Patent Number: 4,650,481
[45] Date of Patent: Mar. 17, 1987

[54] CRINKLED, QUILTED ABSORBENT PAD

[75] Inventors: James J. O'Connor, Calumet County; Theodore B. Lang, Winnebago County; Peggy H. Miller, Outagamie County, all of Wis.

[73] Assignee: Kimberly-Clark Corporation

[21] Appl. No.: 704,367

[22] Filed: Feb. 22, 1985

[51] Int. Cl.⁴ ............................................. A61F 13/16
[52] U.S. Cl. .................... 604/380; 604/366; 604/370
[58] Field of Search ............... 604/370, 372, 366, 378, 604/379, 380

[56] References Cited

U.S. PATENT DOCUMENTS

| | | |
|---|---|---|
| Re. 30,972 | 6/1982 | Kyle et al. . |
| 2,670,567 | 3/1954 | Meyer . |
| 3,016,599 | 1/1962 | Perry, Jr. . |
| 3,427,670 | 2/1969 | Nimoy . |
| 3,441,468 | 4/1969 | Siggel et al. . |
| 3,501,369 | 3/1970 | Drelich et al. . |
| 3,691,570 | 9/1972 | Gaines et al. . |
| 3,717,150 | 2/1973 | Schwartz ............................ 604/372 |
| 3,801,420 | 4/1974 | Anderson . |
| 3,881,490 | 5/1975 | Whitehead .......................... 604/380 |
| 3,903,890 | 9/1975 | Mesek et al. ....................... 604/379 |
| 3,927,673 | 12/1975 | Taylor . |
| 3,971,381 | 7/1976 | Gibson . |
| 4,013,816 | 3/1977 | Sabee et al. . |
| 4,100,324 | 7/1978 | Anderson et al. .................. 604/366 |
| 4,115,610 | 9/1978 | Wortman . |
| 4,196,245 | 4/1980 | Kitson et al. . |
| 4,216,774 | 8/1980 | Graber ................................ 604/372 |
| 4,226,238 | 10/1980 | Bianco ................................ 604/372 |
| 4,275,105 | 6/1980 | Boyd et al. . |
| 4,372,312 | 2/1983 | Fendler ............................... 604/370 |
| 4,397,644 | 8/1983 | Matthews et al. .................. 604/370 |

Primary Examiner—C. Fred Rosenbaum
Assistant Examiner—Sherri E. Vinyard
Attorney, Agent, or Firm—P. A. Leipold; D. L. Traut; J. J. Duggan

[57] ABSTRACT

The invention is generally accomplished by providing a pad that has an impermeable backing member, an overlaying permeable member and an absorbent coform layer therebetween. The pad is provided with a quilted pattern by permanent adhering compression of the pad in narrow areas, forming a lined pattern. The pad further may be heated to shrink the coform and provide a pleasing puckered surface.

22 Claims, 9 Drawing Figures

U.S. Patent  Mar. 17, 1987  Sheet 1 of 3  4,650,481
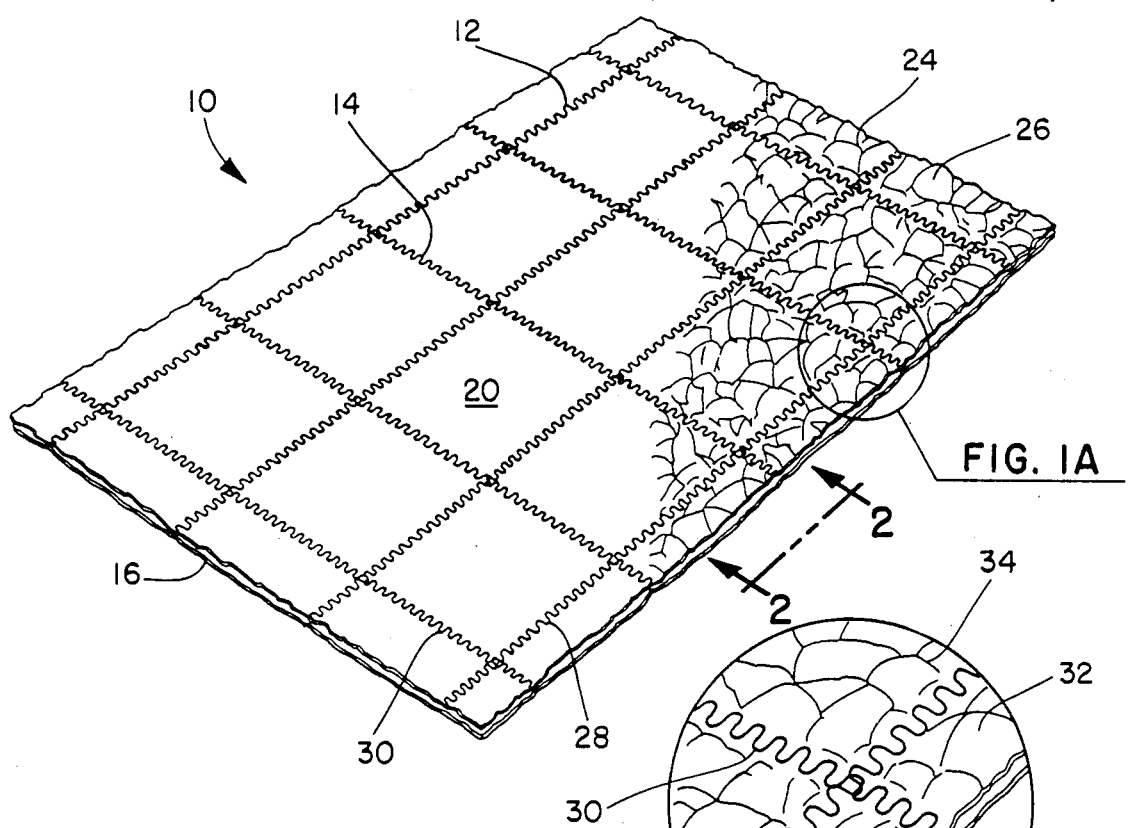
FIG. 1
FIG. 1A
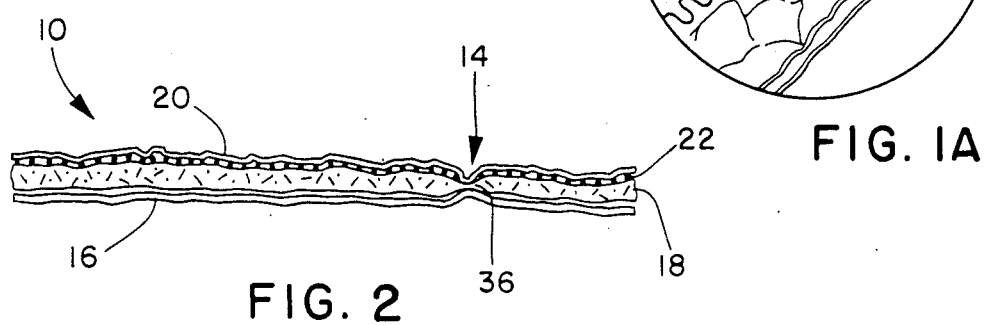
FIG. 2
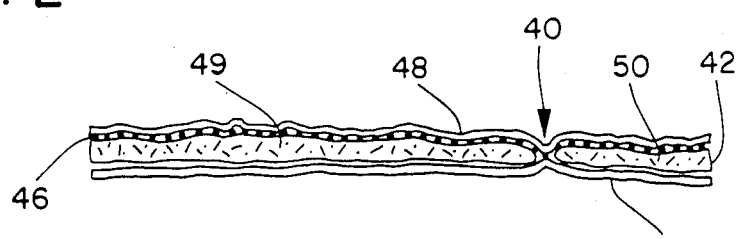
FIG. 3
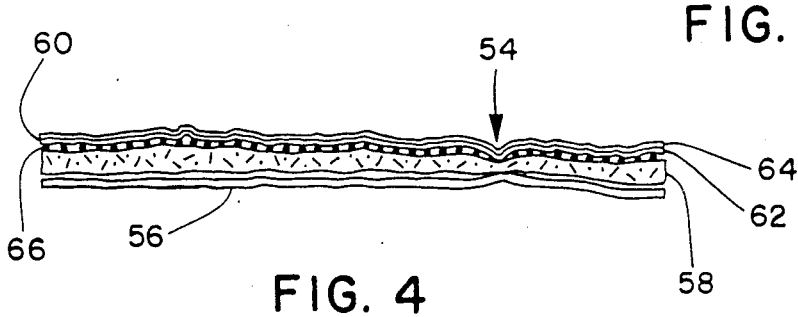
FIG. 4

CRINKLED, QUILTED ABSORBENT PAD

TECHNICAL FIELD

The present invention relates to absorbent pads. It particularly relates to reusable pads having a crinkled surface and a quilted pattern.

BACKGROUND OF THE INVENTION

The use of bed soaker pads has long been known in the art. Such pads often called soaker pads are commonly placed on beds to absorb exudates such as urine, blood and other body fluids that are exuded by bed patients. Such pads may also be placed onto chairs used by incontinent persons or into the clothing used by incontinent persons.

Presently there are several types of pads available for this purpose. A common type of pad is formed from cloth that is washed and reused after it has been soiled. The cloth pads are relatively expensive and due to staining and deterioration do not have a particularly long life. Pads, in use, are often cut to size for specific uses or become so heavily soiled that they must be discarded. The cloth soaker pads may or may not be provided with a rubber backing. The pads both with and without a rubber backing are expensive, particularly when an entire hospital or nursing home must be provided with a multiplicity of pads for each patient in order to provide for laundering of the pads.

Disposable pads for use as soaker pads for protection of beds and chairs are also known. These pads are of several types. One type is formed with an impermeable polymer covering on one surface, divellicated wood fibers as fluff or wadding over the impermeable backing, and a permeable cover of a carded web material or tissue on the side exposed to moisture. These pads have the disadvantage that they are thin and not very absorptive. Further, if they are torn, fluff is released into the environment, causing a housekeeping problem. The loose fluff can be a health hazard, causing cross infection as it provides a mechanism of transport for bacteria, viruses and germs carried from one patient's bed or room to another. Another type of pad is similar to the above-described pad, except that the fluff of wood pulp is held together with adhesive. A third type uses creped tissue sheets as absorbent. The second and third types are expensive and not reusable. A fourth type of pad is formed with a polymer backing that has adhered thereto a coform absorbent structure that is overlaid with a spunbonded permeable member on the side exposed to moisture. Coform is an air-formed blend of polypropylene and divellicated wood fibers. This pad also is not readily washable, as the adhesives holding the coform to the polymer are not especially heat-resistant during drying, and further, the wood fibers leave the coform during washing and form hardened horny balls or nits beneath the permeable cover.

There remains a need for a soaker pad that will be washable, low in cost, and effective. There is particularly a need for such a pad that will inhibit rapid sideways surface transfer of moisture such that moisture will stay within the center target portion of the pad rather than running to and off of one edge causing soiling and staining of the bed linens.

DISCLOSURE OF THE INVENTION

An object of this invention is to overcome disadvantages of prior absorbent pads.

Another object of this invention is to provide a washable coform absorbent pad.

An additional object of this invention is to provide a soaker pad of pleasing appearance and feel.

An additional further object of this invention is to provide a low-cost, quilted absorbent pad.

These and other objects of the invention are generally accomplished by providing a pad that preferably has an impermeable backing member, an overlaying permeable member and an absorbent coform layer therebetween. The coform layer is preferably adhered to the impermeable member to form an integral structure. The pad is further provided with a quilted pattern by permanent adhering compression of the coform, backing member and overlaying member in narrow areas, forming a lined pattern. The pad further may be washed and dried to shrink the coform and provide a pleasing puckered surface with the quilted pattern. The pad alternatively may have a permeable layer on each exterior side with compression zones forming a quilted pattern.

BRIEF DESCRIPTION OF DRAWINGS

FIG. 1 is a view of the pad of the invention with one section shown in exploded view.

FIG. 1A is an exploded view of the portion that is circled in FIG. 1.

FIG. 2 is a view from the edge of the pad of FIG. 1.

FIG. 3 is the cross section of an alternate pad of the invention.

FIG. 4 illustrates in cross section another alternate pad construction of the invention.

MODES FOR CARRYING OUT THE INVENTION

Figure 5:
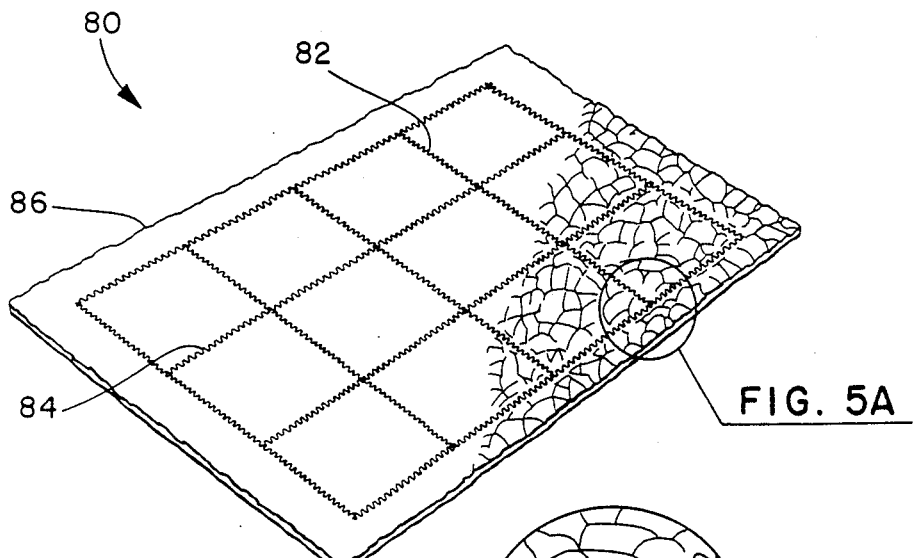
FIG. 5 is a view of an alternate quilting pattern for a pad of the invention.
Figure 5A:
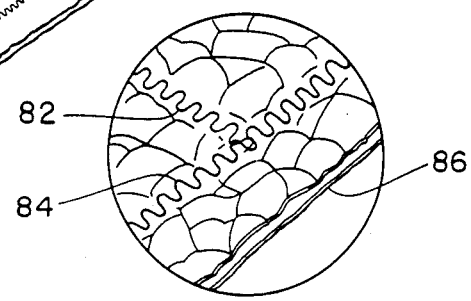
FIG. 5A is an exploded view of the portion circled in FIG. 5.

The invention has numerous advantages over prior art practices. The pad of the invention may be laundered more than ten times for reuse. Further, the pad of the invention is low-cost but will hold together during laundering, become softer, and more pleasing to sight and touch with laundering. Further, the pads of the invention dry faster than ordinary cloth pads, thereby lowering drying costs compared with cloth pads. The pads of the invention are less likely to allow the transmission of urine across their surfaces such that the urine runs off the edge of the pad. Another advantage of the pad of the invention is that the quilted surface of the pad of the invention is more abrasion resistant than previous disposable pads. These and other advantages of the invention will become apparent from the detailed description below.

The pad 10 illustrated in FIG. 1 and in the end view of FIG. 2 is generally composed of three layers—a permeable cover 16, an absorbent inner member 18, and an impermeable backing member 20. The pad is provided with a pattern of quilting lines such as 12 and 14, running in generally perpendicular directions. These quilting lines are areas of compression of the permeable liner and absorbent in longitudinal densified areas approaching the impermeable backing sheet 20. The lines of compression may be formed by ultrasonic bonding, heat and compression, or the use of glue and compression. The method of formation of permanent compression quilting lines will vary, depending on the materials forming the absorbent, permeable cover and pad backing sheet. The absorbent 18 is generally bonded to the backing member 20 by adhesive 22. The adhesive is placed in lines or spread evenly onto the surface of the impermeable backing and the absorbent adhered thereto. The pad is provided on both surfaces with a puckered or crinkled appearance by wetting and drying after formation, such as during washing. This crinkled appearance is provided by valleys 24 and peaks 26.

As seen in the exploded section of FIG. 1, the peaks such as 32 are separated by valleys such as 34. The densified areas of embossing 28 and 30 generally do not have the crinkled system of peaks and valleys. The peaks and valleys are discernible on both the body side and backing side 20 of the sheet, although they are much more prominent on the impermeable backing side 20.

As illustrated in FIG. 2, the embossed section 14 has a section 36 of compressed absorbent. Such an area of compressed absorbent will provide for more rapid transmission of fluid, than the uncompressed areas, as the capillaries are smaller. An alternate structure such as shown in FIG. 3 is formed with an embossed area 40 that results in substantially complete destruction, in the embossed area 40, of the capillaries of the absorbent 42. The area 40 forms a substantially nonporous bonding of the permeable cover 44, absorbent 42, adhesive 46, and backing member 48. Such a structure has the advantage that if it is wetted in the center target area it does not easily transmit wetness to the edge of the pad where it could be squeezed out onto the bed. The moisture will tend to fill absorbent in an area such as 49, prior to crossing compressed area 40 and wetting the absorbent in area 50. An ultrasonic member may be utilized for this fusion. Also, heat and compression or an adhesive and compression may be utilized to provide the compressed areas.

Illustrated in FIG. 4 is an alternative construction. This construction has partially compressed area 54, forming a line of embossing. The structure has permeable member 56 absorbent 58, and backing member 60 that is formed of a two-layer structure, having impermeable layer 62 and a cloth-like member 64 bonded to the impermeable member. The impermeable member 60 is adhered to the absorbent 58 by adhesive 66. This pad is particularly desirable as it presents a more pleasing appearance as the outer surface is cloth-like. A preferred material for such a pad is a coextruded sheet formed by extrusion of polypropylene polymer onto a thin, spunbonded sheet. Such a composite further will become more soft to the touch after washing as some of the pulp fibers are released from the polymer.

FIG. 5 illustrates a pad of the invention having an alternative embossing pattern. In the pad 80 the embossing lines 82 and 84 do not extend to the edge 86 of the pad. This embodiment has the advantage that the compressed areas of absorbent are not able to transmit fluid to the outer edge of the pad, as the compressed areas do not extend to the edge. Therefore, fluid is distributed throughout the embossed section in the middle and wetting of the bed or chair on which the mat is placed is less likely.

Figure 6:
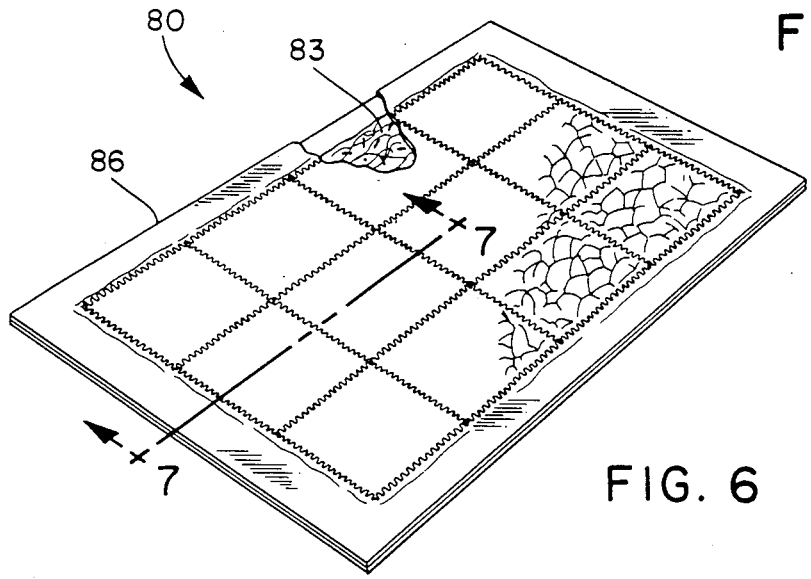
FIG. 6 illustrates a pad of the invention having non-absorbent edges.
Figure 7:
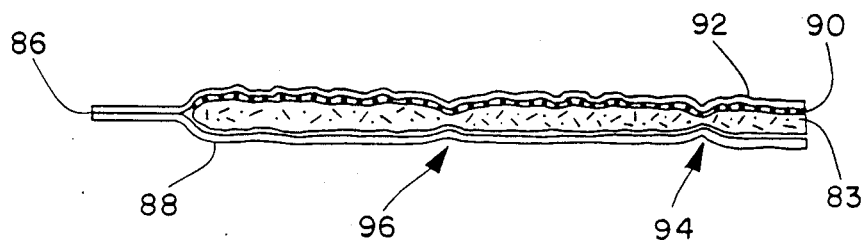
FIG. 7 is a partial cross section of the pad of FIG. 6.

FIGS. 6 and 7 illustrate an alternative pad construction. Pad 80 is less likely to leak at the edges than a pad such as in FIG. 1. The pad 80 has absorbent 83 centered and not extending completely to the edge 86 of the pad. The pad is of the same structure as earlier indicated with permeable member 88 overlaying the absorbent 83. The absorbent 83 is adhesively attached by adhesive 90 to an impermeable backing sheet 92. The pad in the area of the absorbent 83 is provided with a quilted pattern of densified area such as 94 and 96 in FIG. 7. This pad also preferably has the crinkled polymer surface of the earlier described pads of the invention.

Figure 9:
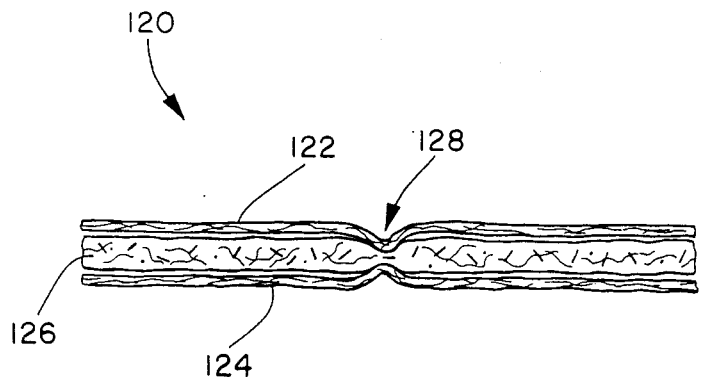
FIG. 9 is a partial cross section of an alternate pad in accordance with the invention.

In an alternate form of the invention the pad may be formed with a permeable layer on both sides. FIG. 9 illustrates in cross section such a soaker pad 120 with a permeable layer on each side. The layers 124 and 122 are of permeable material such as spunbonded polypropylene webs. The absorbent 126 is preferably the coform absorbent of air-formed polypropylene and wood fibers earlier discussed. The layers are bonded at area 128 as part of a quilting pattern. The quilting may be carried out with ultrasonic bonding, with adhesive bonding, or sewing to form a variety of patterns. The alternative pads with permeable covers would find use as reusable soaker pads. For instance, the pads would be used when an entire or large portion bed was covered with an impermeable sheet. The pads would absorb liquids deposited onto the sheet before they could run off the sheet.

The pads of the invention surprisingly have been found to be washable more than ten times with gentle laundering and air drying or drying in conventional laundry equipment at low temperatures. Prior bed pads have been formed from similar structures without the quilting of the coform as in the invention. However, the quilting prevents the formation of horny balls or nits of wood fiber during laundering. Such nits or balls would form under the permeable cover member of prior pads and cause the pads to be both unsightly and possibly uncomfortable to the person using the pad.

The absorbent material of the invention is a coform material. Coform is an air-formed mixture of stable fibers and meltblown continuous fibers. The formation of coform is disclosed in U.S. Pat. No. 4,100,324—Anderson et al.—that is hereby incorporated by reference. A coform of polypropylene meltblown fibers and divellicated wood pulp has been commercially available for several years. However, as stated above, when this material was washed after being formed into a pad, wood fibers would leave the material and form horny balls under the permeable layer. These hardened balls were unsightly and uncomfortable. In the instant invention, the quilting of the pad prevents the formation of the balls as there is not sufficient loose wood fiber available within each fastened area between the quilting lines to allow formation of such horny balls or nits during washing.

An additional invention benefit in the adhesive connection of the coform to the permeable sheet followed by quilting is that when the material is subjected to heat, such as during washing and drying, the coform material will shrink, forming a very attractive puckered or crinkled surface on the impermeable member as well as to a lesser degree on the body-side. Thus the material becomes more attractive and softer after washing.

The coform utilized in the instant invention may be formed of any combination of meltblown polymer and staple fiber. Typical of suitable meltblown fibers are polyethylene, polyesters, nylon, and other thermoplastic fibers. Typical of the staple absorbent fibers are cotton, polyester, rayon, and nylon. The preferred material of the invention is the air-formed combination of polypropylene meltblown with divellicated wood pulp fibers commonly referred to as coform. This combination is preferred as it shrinks by an amount that gives an attractive surface texture without being significantly smaller and further is very absorbent and is low in cost.

The ratio of staple fiber to meltblown continuous fiber may be any desired ratio. Generally the more meltblown utilized in relation to the total, the higher the cost and less the absorbency. The countervailing consideration is that the greater the amount of staple fiber, the higher the absorbency but the lower the strength. Generally it is preferred that the meltblown polypropylene be present in an amount between about 30 and about 40 percent, and the divellicated wood fiber be present in an amount between 60 and 70 percent for high absorbency and strength sufficient for washing and reuse. The formation of the air-formed combinations of meltblown fibers and staple fibers are known and are disclosed in U.S. Pat. No. 4,100,324, Anderson et al.

The impermeable backing sheet may be of any desired construction that is impermeable to the passage of liquids. Typical of such materials are polymer films such as copolymers of ethylene and vinylacetate, nylon, and polyesters. Preferred are films of polyethylene or polypropylene as these are low in cost and reasonable strong at thin film thicknesses. A particularly preferred material for the impermeable backing sheet is a composite structure of an impermeable film such as polypropylene and a lightweight spunbonded fabric. Such a material is impermeable, strong, and provides a pleasing cloth-like outer surface. A suitable material is disclosed in U.S. Ser. No. 670,350 filed Jan. 10, 1985 by inventor P. T. VanGompel.

The quilting of the pad of the invention may be carried out in any desired manner. Typical of methods of applying quilting to a pad in accordance with the invention is the use of heat and pressure, ultrasonics, and adhesives. It is possible that if quilting is done immediately after formation that the adhesives that adhere the coform absorbent material to the backing may be sufficient to also permanently bond and hold the quilting pattern. The use of heat and pressure in forming the quilting pattern is also suitable as the materials forming the preferred pad of the invention are thermoplastic and may be compacted and adhered by heat and pressure. The use of ultrasonics to provide the quilted areas also is possible. The combination of ultrasonics with adhesives immediately after formation may be particularly desirable. The particular quilting method may depend upon the process by which the pad is formed, as well as the pad materials and construction method utilized. For instance, if the quilting is performed immediately after formation, the glue may still be in a state to aid in quilting whereas if quilting is performed much later in time on a separate forming line, the glue may be hardened and less likely to be an aid in quilting.

The absorbent material may be any desired thickness, weight and material to provide the absorbency desired for the particular product. In a typical bed pad utilizing the preferred coform of polypropylene and wood fibers, the absorbent thickness is generally between about 0.05 and about 0.5 inch. The preferred pad has an absorbent thickness between about 0.1 and about 0.2 inch to provide a pad with sufficient absorbency, washability, and pleasing quilted effect.

Pads of the invention may be made in any desirable size. Typically bed pads are between about 18 by 18 inches, and about 2 feet by 3 feet. Chair pads generally are close to square in the range of between about about 17 and about 23 inches. Bed pads usually are about 2 feet by about 3 feet.

In the preferred pad of the invention the coform that is adhered to the impermeable backing sheet shrinks somewhat upon laundering. The shrinkage occurs when the pad is washed and dried. Further, in formation of pads of the invention, it may be desirable to shrink the pad on the assembly line such that it already has the puckered appearance prior to the customers' use. The shrinkage of the coform provides the pad with a rough, crinkled or puckered surface having irregular patterns of surface rugosities. The pad typically will shrink between about 15 and about 20 percent in each direction. This leads to a total area reduction of about 33 percent. However the absorbency of the pad is not significantly affected. The pad after several washings may have lost about 7 percent by weight. The amount of weight lose will depend on polypropylene to wood fiber ratio of coform and the weight and openness of the permeable cover sheet. This weight lost is attributed to the loss of cellulose fibers. The washing of the pad produces a softer surface on the spunbonded permeable body side member. This softer surface is particularly desirable in not abrading the skin of the user.

The following example is intended to be illustrative and not limiting as to the method of formation of pads in accordance with the invention. It being understood and as set forth above, there are a variety of alternative methods and materials that may be used in the pads of the invention.

A spunbonded polypropylene permeable member having a weight of about 0.4 ounces per square yard is provided on the foraminous belt of a coform machine. Meltblown polypropylene is formed and deposited onto the spunbonded polypropylene sheet as it moves below the meltblown nozzles on the machine and as the meltblown polypropylene is formed, divellicated wood fibers are blown into the air stream containing the just-formed meltblown fibers in accordance with the method of the earlier-cited Anderson patent. The weight ratio of the divellicated wood fibers to meltblown is about 70 percent wood fibers and about 30 percent meltblown polypropylene. The coform is collected onto the spunbonded material on the foraminous belt and becomes mechanically attached thereto in a layer about 0.2 inch thick. The composite of coform with the spunbonded cover is brought into contact with an adhesively-coated polymer sheet. The polymer sheet of about 2 feet by 3 feet is polypropylene sheet of about 750 microns thickness having coated thereon a Findley 952-383 polyvinyl acetate copolymer emulsion adhesive by print roll at an amount of about 8 grams per square meter. The composite of spunbond and coform is brought into contact with the polymer sheet such that the coform side contacts the adhesive. The pad is then embossed with a known ultrasonic embossing device ordinarily referred to as an ultrasonic sewing machine, having a rotary anvil. This device is used to form a quilting pattern of rectangles of about 1⅜ inches by 1¾ inches. The ultrasonic bonding is done in a serpentine pattern of a width of about 174 inch. The serpentine pattern is illustrated in FIG. 1. The pad is then gently washed with a home laundry detergent and dried at a medium drying temperature of about 110° F. temperature.

The pad recovered after drying has a pleasing crinkled and puckered polymer sheet surface, with the rugosities also forming a somewhat less defined but visible pattern of roughness on the absorbent side of the pad.

The absorbent pads of the invention may be utilized to form a variety of articles. The properties of reusability, high absorbency and abrasion-resistance are desirable for many uses. Typical of such uses are bed pads, playpen liners, body changing pads, nursing pads, floor mats, shower pads, canning pads, protective garments, tablecloths, and paint cloths. The material further may be shaped to form garments such as incontinent garments, catamenial devices or diapers.

Figure 8:
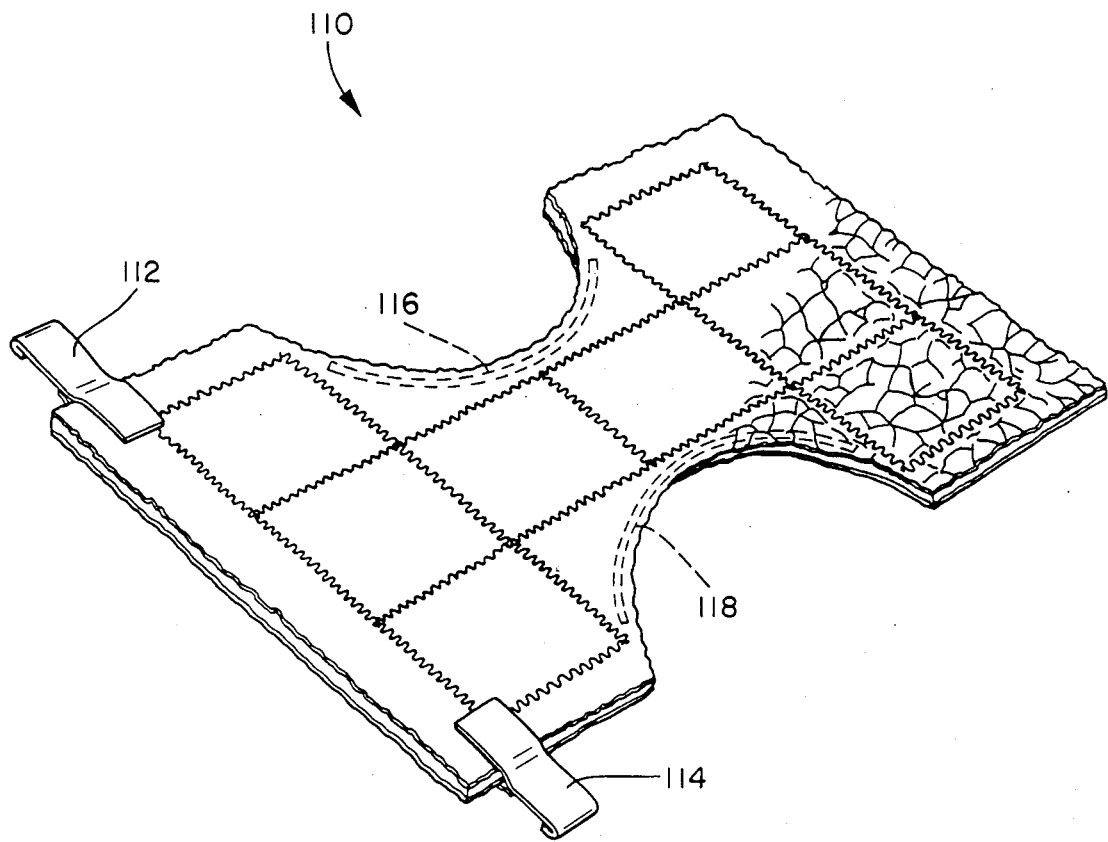
FIG. 8 is a plan view of a garment in accordance with the invention.

FIG. 8 is illustrative of a garment formed from a pad of the invention such as the pad of FIG. 5. The garment is an incontinent adult garment 110, having tapes for fastening 112 and 114. The garment further has leg elastics 116 and 118 that provide sealing from leakage. Such a garment also would be particularly desirable for toilet training of children where the garment could be washed and reused. Further it could be used for adult incontinent patients with washing of at least about 10 times to lower the cost of the garment. By cutting and shaping, a variety of garments and shaped pads, may be formed from the pleasing and reusable pads of the invention.

The foregoing specification is intended to be illustrative and not exhaustive in describing the embodiments possible within the scope of the invention. For instance, the pad of FIGS. 6 and 7 could be formed with very wide nonabsorbent edges such that it could be used as a bed pad with tucking of the nonabsorbent long pieces under the mattress to hold the pad in place. The scope of the invention is intended to be limited by the scope of the claims attached hereto.

I claim:

1. A washable absorbent pad comprising a backing sheet, a body-side permeable cover, an absorbent coform member located between said permeable cover and said backing sheet wherein said pad is provided with a pattern of narrow densified areas by permanent compression of said coform absorbent, wherein said densified areas form a quilted pattern embossed onto said pad, and said body-side cover, said backing sheet and said coform are permanently adhered together in said densified areas.

2. The washable pad of claim 1 wherein said pad has been heated to shrink said coform, thereby providing an irregularly puckered surface.

3. The washable pad of claim 1 wherein said backing sheet is larger than said absorbent.

4. The pad of claim 1 wherein said densified regions increase lateral liquid transfer.

5. The pad of claim 1 wherein said backing sheet is impermeable.

6. The pad of claim 5 wherein said absorbent member is adhered to said impermeable backing sheet by adhesive.

7. The pad of claim 1 wherein said quilted pattern comprises densified areas adhesively secured by an adhesive utilized to adhere said coform to said backing sheet.

8. The pad of claim 1 wherein said densified areas are heat sealed.

9. The pad of claim 1 wherein said densified areas will transmit fluid.

10. The pad of claim 2 wherein said densified areas are substantially permeable.

11. The pad of claim 1 wherein said densified areas are substantially permeable.

12. An absorbent mat comprising an impervious backing sheet, a pad of coform absorbent material adhered to said impermeable backing sheet, and a permeable web adhered to the outer surface of said coform wherein said pad is provided with a series of intersecting densified areas forming a quilted pattern, said backing sheet, said permeable web and said absorbent are permanently adhered together in said densified areas and wherein said mat has a puckered surface.

13. The mat of claim 12 wherein said densified areas transmit fluid.

14. The mat of claim 12 wherein said densified areas are substantially impermeable.

15. A method of forming an absorbent mat comprising providing an absorbent pad of coform material having a permeable cover adhered to a first surface, adhering a sheet to the second surface of said pad, permanently compressing narrow intersecting areas of said pad to adhere together said coform material, said permeable cover and said sheet in densified areas having a quilted pattern.

16. The method of claim 15 further including laundering said pad to shrink said coform and provide a pad with a puckered surface.

17. The method of claim 15 wherein said sheet on said second surface is impermeable.

18. The method of claim 15 wherein said permanently compressing is performed using ultrasonic energy.

19. The method of claim 15 wherein said permanently compressing is performed using adhesive to obtain permanent bonding.

20. The method of claim 15 wherein said permanently compressing permanently adheres said first sheet, said second sheet and said absorbent pad together in a quilted pattern.

21. The pad of claim 1 wherein said backing sheet is permeable.

22. The pad of claim 1 wherein said densified areas are substantially impermeable.

* * * * *